(12) United States Patent
Weiss

(10) Patent No.: US 7,485,878 B2
(45) Date of Patent: Feb. 3, 2009

(54) LASER MICRODISSECTION UNIT

(75) Inventor: Albrecht Weiss, Linden (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 76 days.

(21) Appl. No.: 11/360,940

(22) Filed: Feb. 23, 2006

(65) Prior Publication Data

US 2006/0186349 A1 Aug. 24, 2006

(30) Foreign Application Priority Data

Feb. 24, 2005 (DE) .................. 10 2005 008 925

(51) Int. Cl.
*G01J 1/58* (2006.01)
(52) U.S. Cl. .................................. 250/486.1
(58) Field of Classification Search ............... 250/486.1
See application file for complete search history.

(56) References Cited

U.S. PATENT DOCUMENTS

| | | | |
|---|---|---|---|
| 6,251,467 B1 * | 6/2001 | Liotta et al. | 427/2.11 |
| 6,469,779 B2 | 10/2002 | Baer et al. | 356/36 |
| 6,690,470 B1 * | 2/2004 | Baer et al. | 356/417 |
| 6,790,636 B1 * | 9/2004 | Star et al. | 435/40.5 |
| 7,151,633 B2 | 12/2006 | Storz et al. | |
| 2002/0020800 A1 | 2/2002 | Knebel et al. | |
| 2002/0058300 A1 * | 5/2002 | Yokota et al. | 435/40.5 |
| 2003/0011772 A1 * | 1/2003 | Abe et al. | 356/417 |
| 2003/0197119 A1 * | 10/2003 | Engelhardt | 250/234 |
| 2003/0206296 A1 * | 11/2003 | Wolleschensky et al. | 356/317 |
| 2004/0027683 A1 * | 2/2004 | Dietzsch et al. | 359/655 |
| 2004/0084426 A1 | 5/2004 | Okada | 219/121.68 |
| 2004/0095576 A1 * | 5/2004 | Wolleschensky | 356/317 |
| 2004/0252379 A1 | 12/2004 | Weiss | |
| 2005/0024721 A1 | 2/2005 | Storz et al. | |
| 2005/0103973 A1 * | 5/2005 | Abe | 250/201.3 |
| 2006/0087643 A1 * | 4/2006 | Donovan et al. | 356/36 |
| 2006/0179992 A1 * | 8/2006 | Kermani | 83/651 |
| 2007/0051869 A1 | 3/2007 | Knebel | |

FOREIGN PATENT DOCUMENTS

DE 698 14 041 T2 1/2004
DE 103 00 091 A1 7/2004

(Continued)

OTHER PUBLICATIONS

Fini et al., Immunostaining and Laser-Asisted Cell Picking for mRNA Analysis,2000,Lab. Invest.,80(3),p. 332.*
Brochure: Leica AS LMD, Laser Microdissection System, Leica Microsystems Wetzlar GmbH, Ernst-Leitz-Str. 17-37, D-35578 Wetzlar (Germany), 2000.
European Search Report, mailed Oct. 6, 2006 which issued during the prosecution of PCT Application No. EP 06 10 0924, which corresponds to the present applciation.
Brief translation of European Search Report, Application No. EP 06 10 0924.

* cited by examiner

*Primary Examiner*—David P Porta
*Assistant Examiner*—Djura Malevic
(74) *Attorney, Agent, or Firm*—Darby & Darby

(57) ABSTRACT

A laser microdissection unit for cutting a microscopic sample using a laser beam of a laser includes a microscope and a fluorescence device. The microscope includes an illumination beam path directed onto the sample, and an imaging beam path configured to image the sample. The fluorescence device includes an excitation filter, a dichroic beam splitter, and a blocking filter. The dichroic beam splitter and the blocking filter are spectrally transparent to the laser beam, and the laser beam is directable through the dichroic beam splitter and the blocking filter onto the sample.

13 Claims, 3 Drawing Sheets

LASER MICRODISSECTION UNIT

CROSS REFERENCE TO RELATED APPLICATIONS

This application claims priority to German patent application 10 2005 008 925.9, filed Feb. 24, 2005, the entire subject matter of which is hereby incorporated by reference herein.

FIELD OF THE INVENTION

The invention relates to a laser microdissection unit that cuts a microscopic sample using a laser beam of a laser, which unit includes a microscope having an illumination beam path directed onto the sample and having an imaging beam path that images the sample, and includes a fluorescence device that comprises an excitation filter, a dichroic beam splitter, and a blocking filter.

BACKGROUND OF THE INVENTION

"Laser microdissection" refers to a method with which, in the field of medicine and microbiology, a small piece (called the "dissected specimen") is cut out of a usually planar sample, for example cells or a tissue section, using a finely focused laser beam. The cut-out piece is then available for further biological or medical, for example histological, examinations. A laser microdissection unit of the kind just recited comprises a microscope having an illumination beam path directed onto the sample, and an imaging beam path that images the sample. A laser supplies a laser beam that is coupled into the microscope and directed onto the sample. With the focused laser beam, a piece is cut out of the sample. The laser microdissection unit furthermore encompasses a fluorescence device that comprises, in known fashion, a dichroic beam splitter and a blocking filter.

One such unit is, for example, the Leica AS LMD of Leica Microsystems Wetzlar GmbH. It comprises an upright microscope into whose optical incident-light axis the laser beam is coupled and is directed from above through the objective onto the sample to be cut. The incident-light axis, with the laser beam passing through it, can comprise lenses, diaphragms, or beam scanners for the laser beam, and is therefore also referred to as a "microdissection beam path." An additional fluorescence axis is arranged above the incident-light axis. This fluorescence axis encompasses the complete fluorescence illumination system with a light source and optical system, as well as the conventional fluorescence cube with an excitation filter, dichroic beam splitter, and blocking filter. The arrangement of the fluorescence axis above the microdissection beam path allows simultaneous fluorescence observation and microdissection. The fluorescence axis is manually operated (e.g. switched over). Because the fluorescence axis is placed onto the microscope above the microdissection beam path, no installation space or access exists for motorizing the switchable components in the fluorescence axis.

Other research microscopes possess a higher degree of automation, also providing motorized and/or automated switchovers of components of the fluorescence axis. These research microscopes having a higher degree of motorization or automation therefore usually contain a fluorescence axis integrated into the stand. A laser cannot then, however, be coupled in.

SUMMARY OF THE INVENTION

It is therefore an object of the present invention to provide a laser microdissection unit that permits integration of a microscope having a motorized, integrated fluorescence axis.

The present invention provides a laser microdissection unit that cuts a microscopic sample using a laser beam of a laser, which unit includes a microscope having an illumination beam path directed onto the sample and having an imaging beam path that images the sample, and includes a fluorescence device that comprises an excitation filter, a dichroic beam splitter, and a blocking filter. The dichroic beam splitter and the blocking filter are spectrally transparent to the laser beam.

Dichroic beam splitters and blocking filters of fluorescence filter systems are usually not transparent to wavelengths of the laser, which is typically a UV laser with a wavelength of, for example, 337 nm (nanometers). The laser beam therefore does not go through a fluorescence filter system positioned in the beam path, as is known in the existing art. With an integrated fluorescence axis in the microscope, simultaneous fluorescence observation and microdissection were therefore not hitherto possible. The configuration of the laser microdissection unit according to the present invention now solves this problem by the fact that a special fluorescence filter system is provided. For that purpose the dichroic beam splitter and the blocking filter, in addition to their usual transmissive region for fluorescence illumination and fluorescence imaging, must also be spectrally transparent in the wavelength region of the UV laser that is used.

The laser beam is then directed through the blocking filter and the dichroic beam splitter onto the sample. This allows fluorescence observation of the sample, and cutting of the sample using the laser beam, to be performed simultaneously. For the user, this results in greatly improved capabilities for distinguishing a wide variety of sample regions (e.g. cell types, cell components, etc.) and selecting them for microdissection.

In an advantageous embodiment of the laser microdissection unit, the laser beam of the laser is coupled into the imaging beam path of the microscope using a second dichroic beam splitter, and directed onto the blocking filter.

A configuration of the laser microdissection unit that is particularly service-friendly and also suitable for retrofitting of an existing microscope is achieved by the fact that a separate microdissection beam path is associated with a microscope outside the existing illumination beam path having the fluorescence device. The microdissection beam path guides the laser beam onto the blocking filter and in that fashion couples it into the illumination beam path. Lenses acting on the laser beam, and/or an aperture diaphragm, and/or a second dichroic beam splitter for deflecting the laser beam can be provided in the microdissection beam path.

It proves to be particularly maintenance-friendly and service-friendly if the microdissection beam path is combined into one structural unit that can be placed onto the microscope via at least one alignment surface. It also proves to be advantageous if the microdissection beam path is already optically and mechanically prealigned in the structural unit. The fact that the structural unit and the microscope comprise high-precision alignment surfaces allows the structural unit to be placed in alignment-free fashion onto the microscope.

The laser microdissection unit according to the present invention can be implemented using both an inverted microscope and an upright microscope. For routine examinations, for example in the field of pathology, it proves to be advantageous if the sample can be stained with multiple fluorescent dyes. This then permits spectral multi-band fluorescence observation. Typical fluorescent dyes are, for example, DAPI, FITC, and Texas Red. Because the dichroic beam splitter and the blocking filter that are spectrally transparent to the laser beam, as well as the excitation filter, exhibit transmissivity properties that permit simultaneous spectral multi-band fluorescence observation, sample recovery by laser microdissection is likewise simultaneously possible.

BRIEF DESCRIPTION OF THE DRAWINGS

The invention will be explained below on the basis of an exemplifying embodiment, referring to the schematic drawings in which.

DETAILED DESCRIPTION OF THE INVENTION

Figure 1:
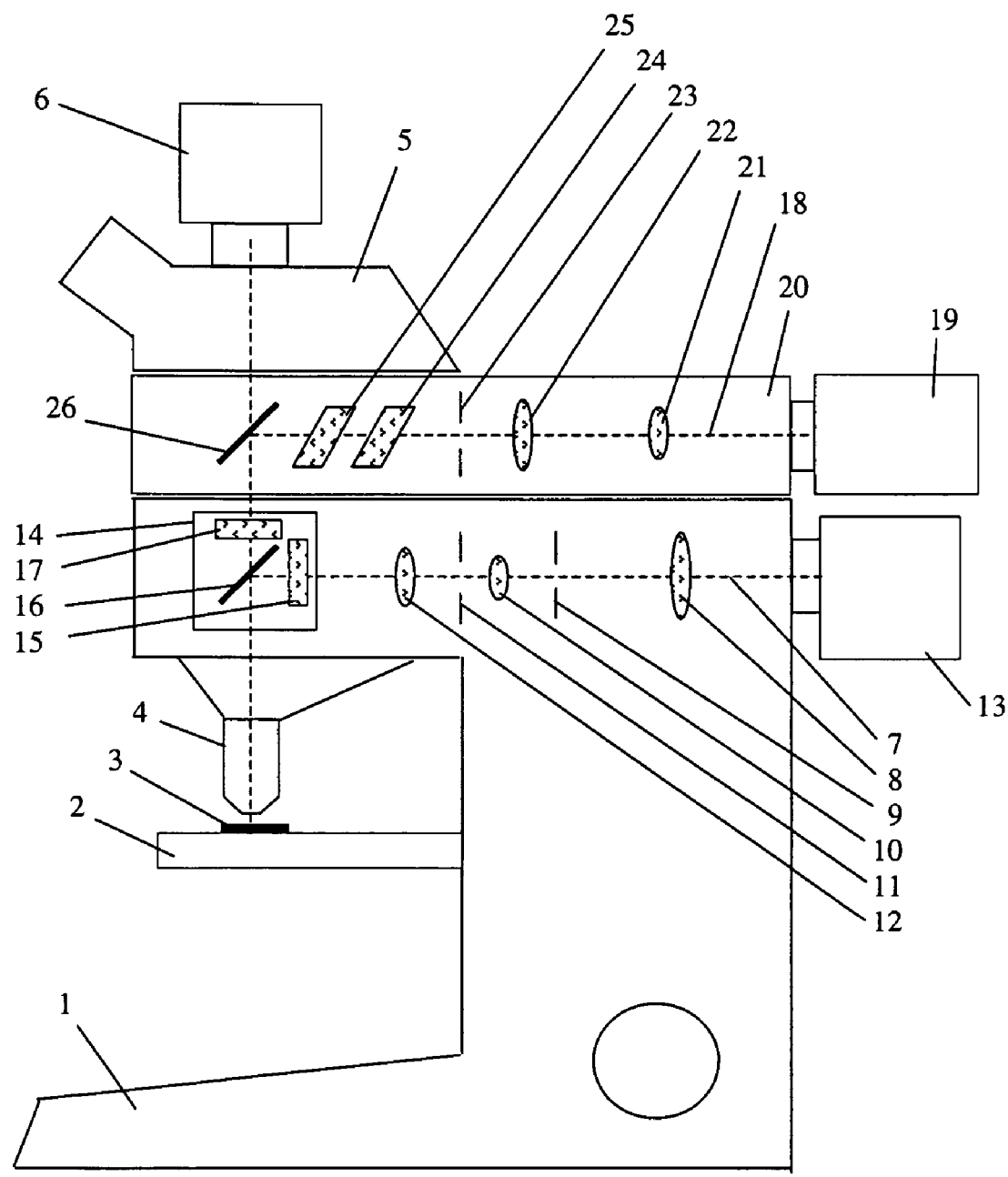
FIG. 1 shows a laser microdissection unit.

FIG. 1 shows a laser microdissection unit with a microscope 1. Sample 3 is arranged on microscope stage 2, and is imaged through an objective 4 and a tube 5 onto a camera. Microscope 1 comprises an integrated fluorescence axis 7 in which a lens 8, an aperture diaphragm 9, a lens 10, a field diaphragm 11, and a lens 12 are arranged. The illuminating light proceeding from lamp housing 13 passes along integrated fluorescence axis 7 and strikes fluorescence device 14. The latter encompasses an excitation filter 15, a dichroic beam splitter 16, and a blocking filter 17, which are spectrally matched to at least one fluorescent dye and its fluorescence band.

A microdissection beam path 18 with a UV laser 19 is arranged above integrated fluorescence axis 7. Microdissection beam path 18 is arranged in a structural unit 20 that is placed onto microscope 1, above integrated fluorescence axis 7, as an attachment.

The laser beam proceeding from UV laser 19 travels, in microdissection beam path 18, through a first lens 21 and a second lens 22, an aperture diaphragm 23, and a first scanner prism 24 and second scanner prism 25. The laser beam then strikes dichroic splitter 26 and is deflected by it to blocking filter 17. Blocking filter 17 and dichroic beam splitter 16 in fluorescence device 14 are spectrally transparent to the laser beam. The laser beam thus passes through fluorescence device 14 and is focused by objective 4 onto sample 3. Desired sample regions are cut out of the sample using the focused laser beam. During the cutting operation, it is possible simultaneously to observe the fluorescence image acquired by camera 6.

Figure 2:
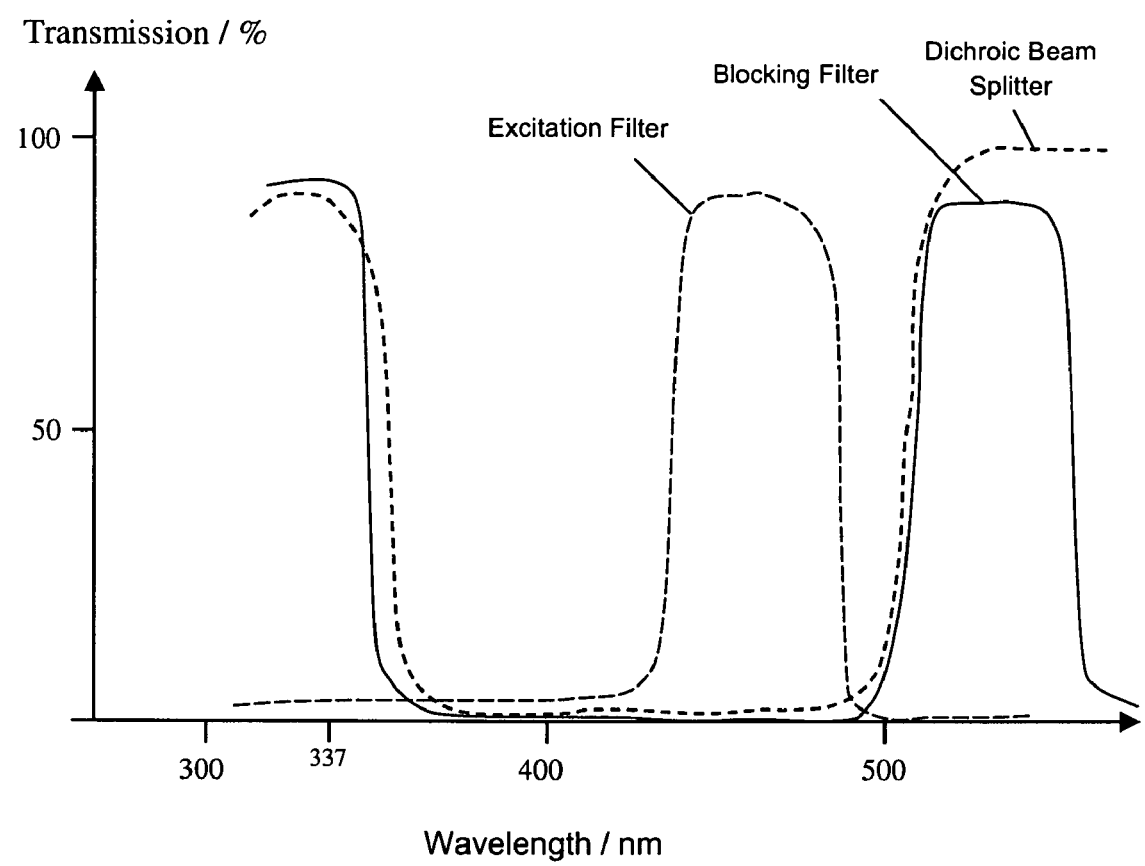
FIG. 2 shows the transmissivity curves of the excitation filter, the blocking filter, and the dichroic beam splitter for a single fluorescent dye.

FIG. 2 shows the transmissivity curve as a function of wavelength (in nanometers) for excitation filter 15, blocking filter 17, and dichroic beam splitter 16. The laser wavelength in the present case is 337 nanometers. The excitation filter has only a single transmissivity band, which is matched to an associated fluorescent dye. The blocking filter is not transparent in this region, but rather has a transmissivity band in the region of the long wavelengths produced by fluorescence. The blocking filter additionally exhibits high transmissivity for the wavelength region around 337 nm (nanometers), i.e. for the wavelength of the UV laser. Adaptations to other laser wavelengths are, of course, possible. Dichroic beam splitter 16 is also transparent in the region of the emitted fluorescent light, i.e. in the same region as blocking filter 17. In addition, both dichroic beam splitter 16 and blocking filter 17 have a high transmissivity for the wavelength of the laser beam.

Figure 3:
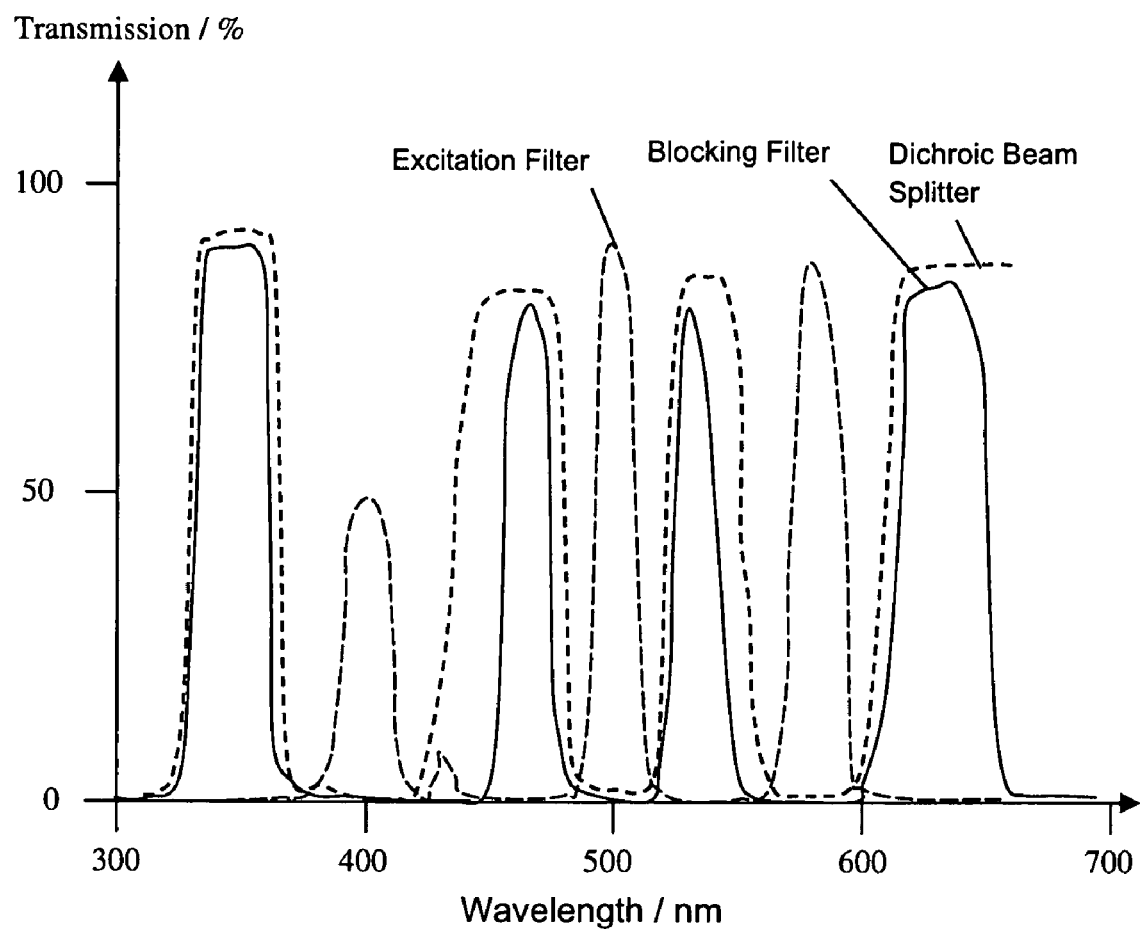
FIG. 3 shows the transmissivity curves of the excitation filter, the blocking filter, and the dichroic beam splitter for multi-band fluorescence using multiple fluorescent dyes.

FIG. 3 shows transmissivity curves as a function of wavelength (in nanometers) for a different filter set of a fluorescence cube that comprises a multi-band excitation filter, a multi-band blocking filter, and a multi-band dichroic beam splitter which have multiple spectral transmissivity bands.

In the present exemplifying embodiment, the multi-band filter system is tuned for combined viewing of multi-band fluorescence resulting from sample staining with three different fluorescent dyes, in the present case DAPI, FITC, and Texas Red. The excitation filter and the blocking filter each exhibit three transmissivity bands for the fluorescence corresponding to the three aforesaid fluorescent dyes. The dichroic beam splitter and the blocking filter furthermore exhibit an additional transmissivity band in the near-UV wavelength region between 337 nm and 355 nm.

The present multi-band filter set is therefore suitable for use with an $N_2$ laser or a solid-state laser. When fluorescence device 14 in microscope 1 of FIG. 1 is operated with a multi-band fluorescence filter set as described here, this therefore permits simultaneous fluorescence observation of sample 3 that is stained with the DAPI, FITC, and Texas Red dyes, concurrently with laser cutting of the sample.

What is claimed is:

1. A laser microdissection unit for cutting a microscopic sample using a laser beam of a laser, the laser microdissection unit comprising:

a microscope including an illumination beam path directed onto the sample, and an imaging beam path configured to image the sample; and a fluorescence device including an excitation filter, a dichroic beam splitter, and a blocking filter;

wherein the dichroic beam splitter and the blocking filter are spectrally transparent to the laser beam and configured to pass the laser beam therethrough onto the sample.

2. The laser microdissection unit as recited in claim 1 wherein the fluorescence device is configured to be activatable at a same time as the cutting of the microscopic sample by the laser beam.

3. The laser microdissection unit as recited in claim 1 further comprising a second dichroic beam splitter configured to couple the laser beam into the imaging beam path and direct the laser beam onto the blocking filter.

4. The laser microdissection unit as recited in claim 3 wherein the fluorescence device is disposed in the illumination beam path, and further comprising a microdissection beam path associated with the microscope and configured to direct the laser beam onto the blocking filter, the microdissection beam path including at least one of a plurality of lenses configured to act on the laser beam;

an aperture diaphragm; and the second dichroic beam splitter.

5. The laser microdissection unit as recited in claim 4 wherein the microdissection beam path is disposed in a structural unit configured to be disposed relative the microscope via at least one alignment surface so that the laser beam passes through the blocking filter.

6. The laser microdissection unit as recited in claim 5 wherein the microdissection beam path is optically prealigned in the structural unit, and wherein the at least one alignment surface includes a first high-precision alignment surface of the structural unit and a second high-precision alignment surface of the microscope, the first and second high-precision alignment surfaces being configured to enable the structural unit to be disposed in aligning-free fashion relative to the microscope.

7. The laser microdissection unit as recited in claim 1 wherein the microscope includes an inverted microscope.

8. The laser microdissection unit as recited in claim 1 wherein the microscope includes an upright microscope.

9. The laser microdissection unit as recited in claim 1 wherein the excitation filter, the dichroic beam splitter, and the blocking filter are each configured to exhibit a respective transmissivity property enabling spectral multi-band fluorescence observation using multiple fluorescent dyes simultaneously.

10. The laser microdissection unit as recited in claim 2 wherein the excitation filter, the dichroic beam splitter, and the blocking filter are each configured to exhibit a respective transmissivity property enabling spectral multi-band fluorescence observation using multiple fluorescent dyes simultaneously.

11. The laser microdissection unit as recited in claim 3 wherein the excitation filter, the dichroic beam splitter, and the blocking filter are each configured to exhibit a respective transmissivity property enabling spectral multi-band fluorescence observation using multiple fluorescent dyes simultaneously.

12. The laser microdissection unit as recited in claim 4 wherein the excitation filter, the dichroic beam splitter, and the blocking filter are each configured to exhibit a respective transmissivity property enabling spectral multi-band fluorescence observation using multiple fluorescent dyes simultaneously.

13. The laser microdissection unit as recited in claim 5 wherein the excitation filter, the dichroic beam splitter, and the blocking filter are each configured to exhibit a respective transmissivity property enabling spectral multi-band fluorescence observation using multiple fluorescent dyes simultaneously.

\* \* \* \* \*